(12) United States Patent
Auld et al.

(10) Patent No.: US 10,111,721 B2
(45) Date of Patent: Oct. 30, 2018

(54) HYBRID ROBOTIC SURGERY WITH MIRRORED AND MIMICKED MOTION

(71) Applicant: Ethicon Endo-Surgery, LLC, Guaynabo, PR (US)

(72) Inventors: Michael D. Auld, Cincinnati, OH (US); Steven G. Hall, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 52 days.

(21) Appl. No.: 14/865,897

(22) Filed: Sep. 25, 2015

(65) Prior Publication Data

US 2017/0086931 A1  Mar. 30, 2017

(51) Int. Cl.
*A61B 34/37* (2016.01)
*B25J 3/00* (2006.01)
*A61B 17/00* (2006.01)
*A61B 34/00* (2016.01)

(52) U.S. Cl.
CPC ........ *A61B 34/37* (2016.02); *A61B 17/00234* (2013.01); *A61B 34/74* (2016.02); *A61B 2017/0003* (2013.01)

(58) Field of Classification Search
CPC ... A61B 34/37; A61B 34/74; A61B 17/00234; A61B 2017/0003
USPC ........................................................ 700/257
See application file for complete search history.

(56) References Cited

U.S. PATENT DOCUMENTS

| | | | | |
|---|---|---|---|---|
| 5,970,457 | A * | 10/1999 | Brant ..................... | A61B 17/00 704/231 |
| 6,132,368 | A * | 10/2000 | Cooper ................. | A61B 46/13 600/102 |
| 7,198,630 | B2 | 4/2007 | Lipow | |
| 7,524,320 | B2 * | 4/2009 | Tierney ................. | G06Q 30/02 606/1 |
| 8,057,410 | B2 * | 11/2011 | Angold ..................... | A61H 3/00 601/35 |
| 8,831,782 | B2 | 9/2014 | Itkowitz | |
| 8,992,422 | B2 * | 3/2015 | Spivey ............. | A61B 17/07207 600/102 |
| 9,301,759 | B2 * | 4/2016 | Spivey ............. | A61B 17/07207 |

(Continued)

FOREIGN PATENT DOCUMENTS

| | | |
|---|---|---|
| WO | 2014151621 A1 | 9/2014 |
| WO | 2014151952 A1 | 9/2014 |

*Primary Examiner* — Michael Collins
(74) *Attorney, Agent, or Firm* — Mintz Levin Cohn Ferris Glovsky and Popeo, P.C.

(57) ABSTRACT

Methods and devices are provided for performing robotic surgery. In general, a surgical system is provided including an electromechanical tool with a first mode of operation in which the electromechanical tool mimics movement of a controller, and a second mode of operation in which the tool mirrors movement of the controller. A hybrid surgical device is also provided including an adapter matable to a handle assembly such that the adapter is electronically coupled to a motor of the handle assembly and is configured to communicate with the motor. A robotic laparoscopic surgical device is also provided including a motion sensor configured to sense movement of an electromechanical tool and an electromechanical arm that assists movement of the tool. A robotic surgical device is also provided including an electromechanical driver associated with a trocar and being configured to rotate and to translate a tool disposed through a passageway.

12 Claims, 8 Drawing Sheets

(56) References Cited

U.S. PATENT DOCUMENTS

| | | | |
|---|---|---|---|
| 2002/0129949 A1 | 9/2002 | Bongers-Ambrosius et al. | |
| 2004/0232892 A1 | 11/2004 | Aradachi et al. | |
| 2005/0261707 A1* | 11/2005 | Schatzberger | A61B 8/0841 |
| | | | 606/130 |
| 2007/0221701 A1* | 9/2007 | Ortiz | A61B 17/068 |
| | | | 227/175.1 |
| 2008/0167662 A1 | 7/2008 | Kurtz | |
| 2009/0118724 A1* | 5/2009 | Zvuloni | A61N 7/02 |
| | | | 606/27 |
| 2009/0202387 A1 | 8/2009 | Dlugos, Jr. et al. | |
| 2011/0046637 A1 | 2/2011 | Patel et al. | |
| 2011/0295242 A1* | 12/2011 | Spivey | A61B 17/07207 |
| | | | 606/1 |
| 2012/0059360 A1 | 3/2012 | Namiki | |
| 2012/0158013 A1 | 6/2012 | Stefanchik et al. | |
| 2012/0199631 A1* | 8/2012 | Shelton, IV | A61B 17/068 |
| | | | 227/176.1 |
| 2012/0199632 A1* | 8/2012 | Spivey | A61B 17/07207 |
| | | | 227/176.1 |
| 2013/0039732 A1 | 2/2013 | Brewer et al. | |
| 2013/0144306 A1* | 6/2013 | Stefanchik | A61B 17/29 |
| | | | 606/130 |
| 2014/0005682 A1* | 1/2014 | Worrell | A61B 18/1442 |
| | | | 606/130 |
| 2014/0094825 A1* | 4/2014 | Flaherty | A61B 19/2203 |
| | | | 606/130 |
| 2014/0151079 A1 | 6/2014 | Furui et al. | |
| 2014/0163664 A1* | 6/2014 | Goldsmith | A61B 17/00491 |
| | | | 623/1.11 |
| 2014/0207124 A1 | 7/2014 | Aldridge et al. | |
| 2015/0025549 A1* | 1/2015 | Kilroy | A61B 19/2203 |
| | | | 606/130 |
| 2015/0038981 A1 | 2/2015 | Kilroy et al. | |
| 2015/0100066 A1* | 4/2015 | Kostrzewski | A61B 34/30 |
| | | | 606/130 |
| 2015/0209059 A1 | 7/2015 | Trees et al. | |
| 2017/0086932 A1* | 3/2017 | Auld | A61B 34/71 |

\* cited by examiner

HYBRID ROBOTIC SURGERY WITH MIRRORED AND MIMICKED MOTION

FIELD OF THE INVENTION

Methods and devices are provided for performing robotic surgery, and in particular for performing hybrid surgery using both manually and robotically operated tools.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. There can be no true force feedback given to the surgeon. Another drawback is the high expense to manufacture such systems.

Accordingly, there remains a need for improved methods, systems, and devices for use in robotic surgery.

SUMMARY OF THE INVENTION

Various methods and devices are provided for performing robotic surgery.

In one embodiment, a surgical system is provided and includes an electromechanical tool, and an electronic control system in electronic communication with the electromechanical tool. The control system is configured to control operation of the electromechanical tool. The system also includes a controller actuable to communicate a control signal to the electromechanical tool via the electronic control system to operate the electromechanical tool. The electromechanical tool can have a first mode of operation in which the electromechanical tool mimics movement of the controller, and a second mode of operation in which the electromechanical tool mirrors movement of the controller.

While the system can have various configurations, in one embodiment the system includes a switch for switching the electromechanical tool between the first and second modes. The switch can be located, for example, on the controller or on a display. The switch can also be configured to disable one or more sensors upon activation. In other aspects, the controller can be configured to wirelessly transmit the control signal.

In another embodiment, a surgical system is provided and includes an electromechanical tool having a handle with an elongate shaft extending therefrom with an end effector on a distal end thereof. A user input device is provided and is configured to receive an input motion from a user. The system also includes a control module electrically coupled to the electromechanical tool and the user input device. The control module can be configured to map the input motion to a first coordinate system. The mapped input motion can be selectively applied to one of a second coordinate system that is identical to the first coordinate system and a third coordinate system that differs from the first coordinate system, and the control module can cause the electromechanical tool to move in coordination with the mapped input motion applied to the selected second or third coordinate system.

In one embodiment, the system can include a switch for switching the control module between a first mode in which the input motion mapped to the first coordinate system is applied to the second coordinate system, and a second mode in which the input motion mapped to the first coordinate system is applied to the third coordinate system. The switch can be located, for example, on the user input device or on a display. The switch can also be configured to disable one or more sensors upon activation. In other aspects, the control signal can be configured to be communicated wirelessly.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, methods and devices for performing hybrid robotic surgery are provided. In particular, the methods and devices disclosed herein allow an operator to perform a surgical procedure using a robotically controlled instrument, and to use a selectively manually operated surgical instrument. The robotic and manual instruments are capable of performing a variety of functions and the procedure can be selectively performed using an entirely manual operation of the instrument(s), a partially-manual and partially-powered operation of the instrument(s), and an entirely powered operation of instrument(s). Manually operated surgical instruments are further provided that are capable of receiving movement assistance from robotic arms during surgery. Robotic trocars are also provided that are capable of receiving instruments and providing controlled movement to those instruments within certain degrees of freedom.

TERMINOLOGY

Figure 1:
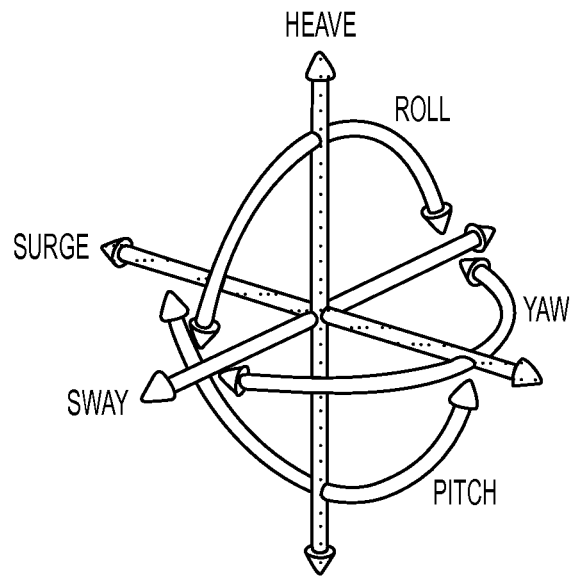
FIG. 1 is a graphical representation of terminology associated with six degrees of freedom.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
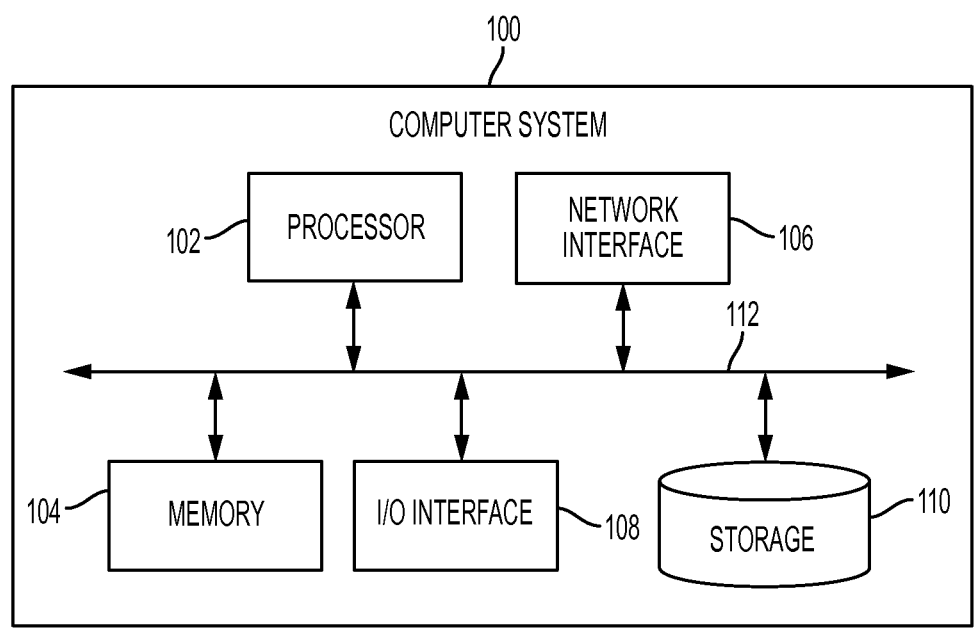
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
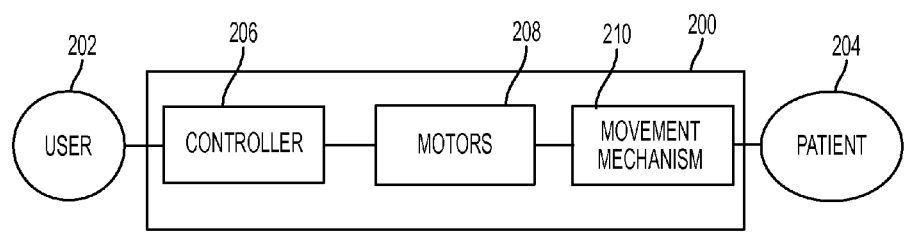
FIG. 3 is a schematic view of one embodiment of a robotic surgical system configured to be operated by a user and to be used during performance of a surgical procedure on a patient.

FIG. 3 schematically illustrates a robotic surgical system 200 configured to be used by a user 202 (e.g., a surgeon, a surgical assistant, etc.) during performance of a surgical procedure on a patient 204. In this illustrated embodiment, the robotic surgical system 200 includes a controller 206, one or more motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument as requested by the user 202. The robotic surgical system 200 can include a plurality of motors, or it can include a single motor. Similarly, the robotic surgical system 200 can include a single controller and a single movement mechanism, or the robotic surgical system can include a plurality of controllers and/or a plurality of movement mechanisms.

In an exemplary embodiment, the movement mechanism 210 includes an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm is configured to provide a plurality of degrees of freedom. More than six degrees of freedom can be provided in a variety of ways, as mentioned above and as will be appreciated by a person skilled in the art. In general, the arm can include a mechanical member configured to move in response to an input received by the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at one or more of the joints.

In an exemplary embodiment, the arm is an electromechanical arm. The electromechanical arm can include one or more mechanical members configured to move in response to an electronic input. Examples of mechanical members that can form the arm include elongate shafts, coupling mechanisms configured to removably and replaceably couple a surgical instrument to the arm, and joints (e.g., hinges, gimbals, etc.). The coupling mechanism can be, for example, clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.

Figure 4:
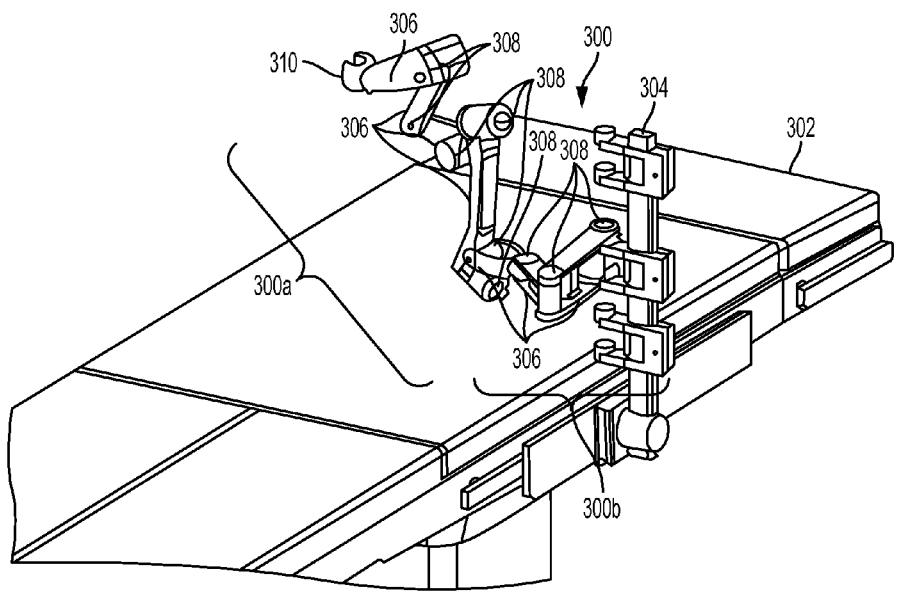
FIG. 4 is a perspective view of one embodiment of an arm of a robotic surgical system, the arm being mounted to a surgical table.
Figure 5:
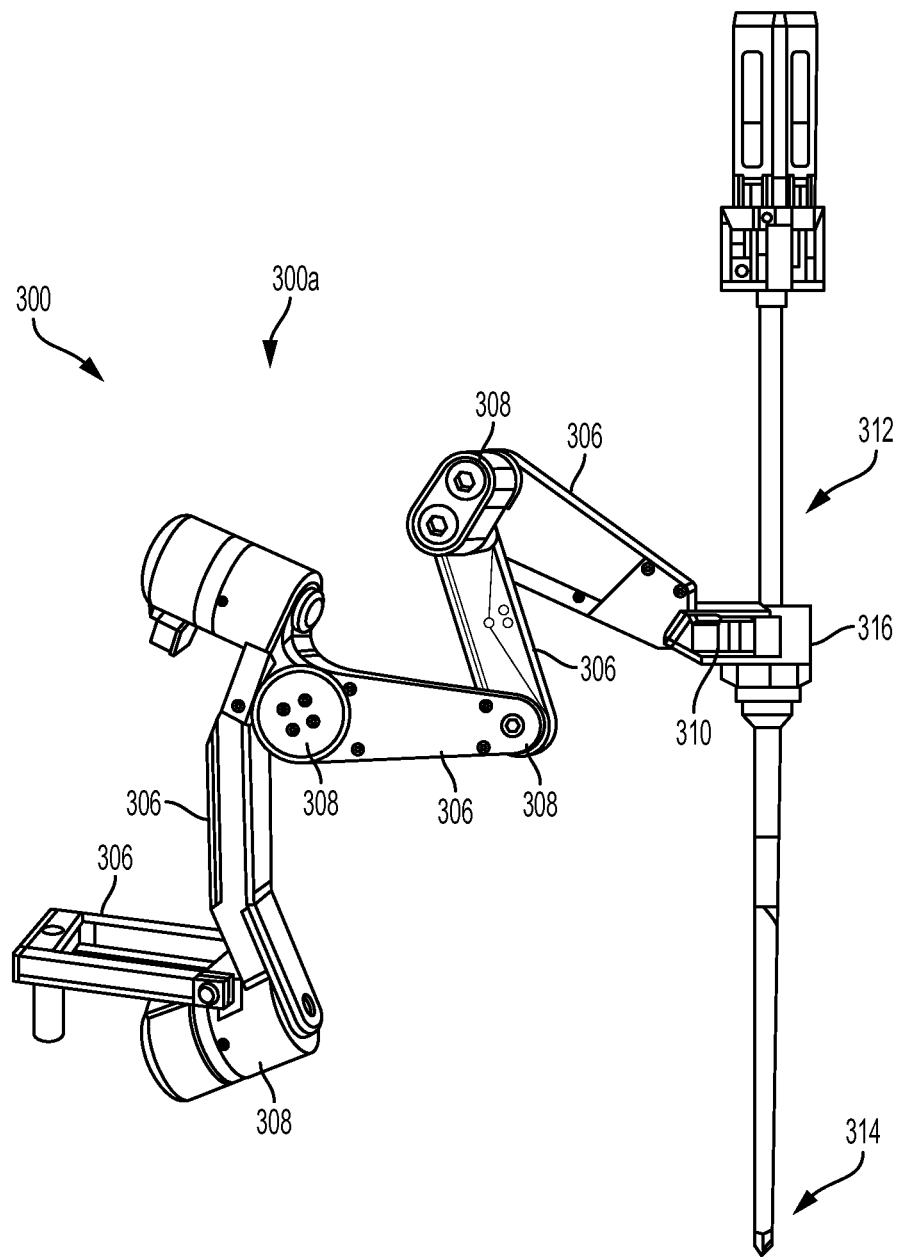
FIG. 5 is a perspective view of an active portion of the arm of FIG. 4 having a tool coupled thereto.

FIGS. 4 and 5 illustrate one embodiment of an arm 300 in the form of an electromechanical arm. The arm 300 in FIG. 4 is shown mounted to a surgical table 302 using a frame 304, however the arm 300 can be mounted to any of a variety of stationary items, a wall, a table, a cart, the ceiling, etc., in any of a variety of ways to help stabilize the arm 300 for use during a surgical procedure. The illustrated arm 300 includes an active portion 300a configured to be actively controlled, e.g., configured to move in response to an electronic input, and a passive portion 300b configured to be passively controlled, e.g., configured to move in response to manual movement thereof. The passive portion 300b can lack motors or other electrical features, while the active portion 300a can include motors and other electrical features that are associated with the joints to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

As shown, the arm 300 can include a plurality of mechanical members 306, a plurality of joints 308, and a coupling mechanism 310. Adjacent ones of the mechanical members 306 can be attached together by a joint 308. In this embodiment, the active portion 300a of the arm 300 includes four mechanical members 306 and five joints 308, the passive portion 300b of the arm 300 includes three mechanical members 306 and three joints 308, and the arm 300 includes another joint 308 between the active and passive portions 300a, 300b. A person skilled in the art will appreciate that the arm can have any number of mechanical members and associated joints in its active and passive portions.

FIG. 5 illustrates the active portion of the arm, and as shown it can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can be configured to facilitate performance of a surgical procedure within the patient. For example, the instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 that is mated to the coupling mechanism 310.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist," which are incorporated herein by reference in their entireties.

Figure 6:
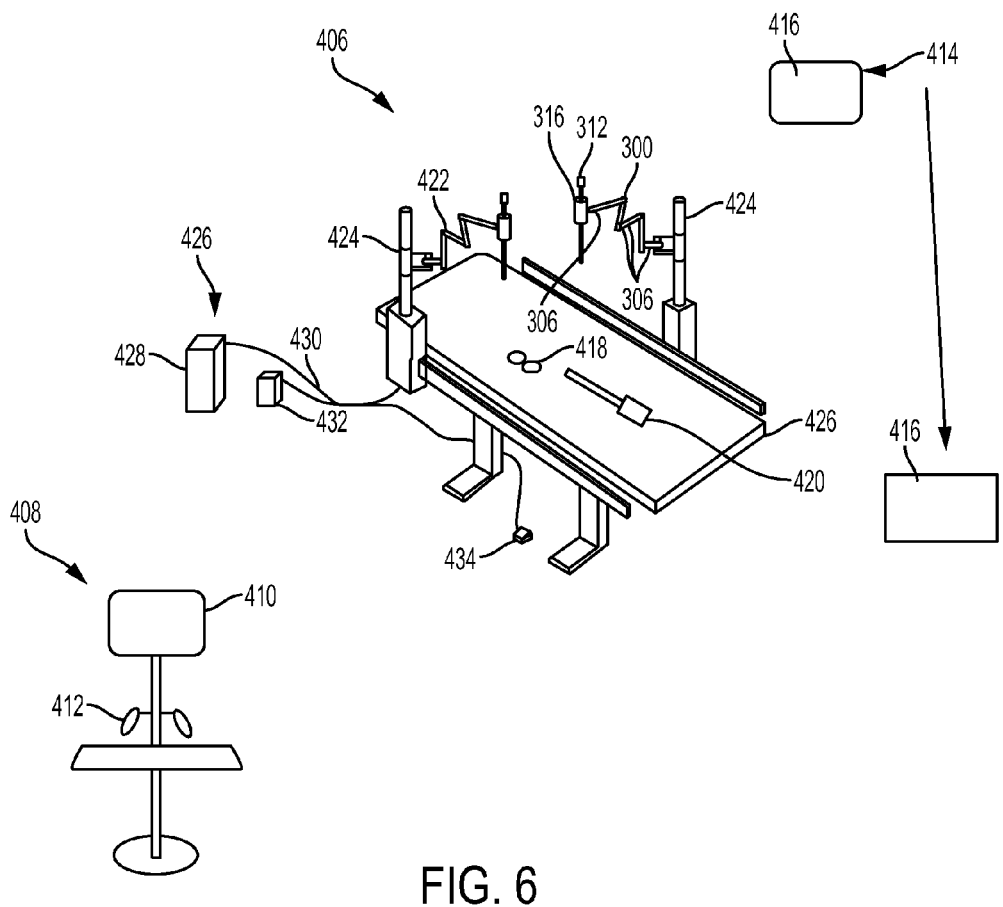
FIG. 6 is a perspective view of another embodiment of a robotic surgical system.
Figure 7:
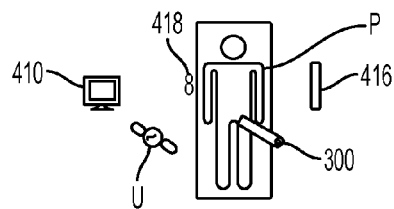
FIG. 7 is a schematic view of the robotic surgical system of FIG. 6 in use during a surgical procedure performed on a patient.
Figure 8:
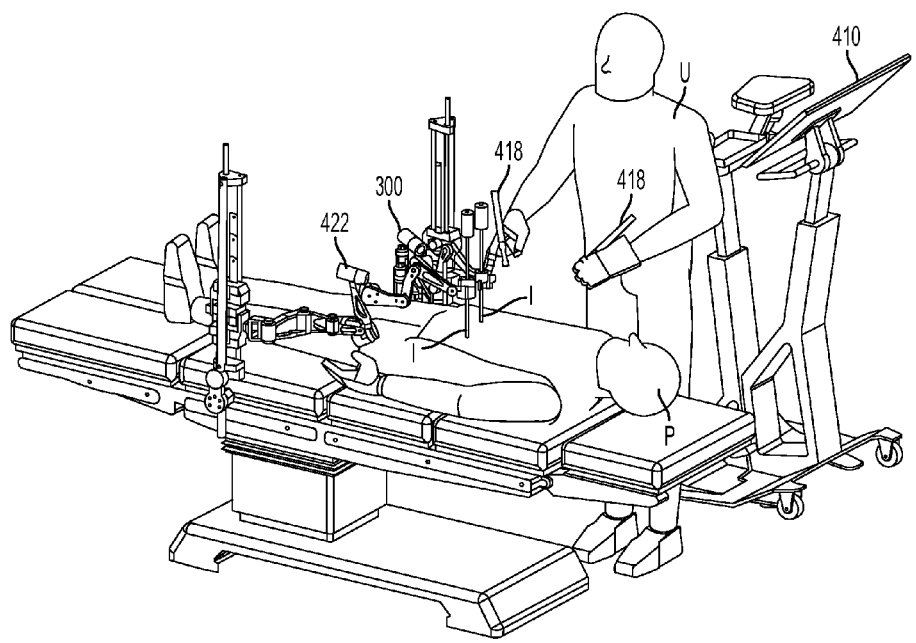
FIG. 8 is a perspective view of the robotic surgical system of FIG. 6 in use during a surgical procedure performed on a patient.

FIGS. 6-8 illustrate the arm 300 coupled to a surgical table. As shown in FIGS. 6 and 7, the arm 300 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input to control movement of the arm 300, a visualization system 414 that can include at least one display 416 configured to display thereon image(s) of a surgical procedure being performed using the system 406, a freely movable user input device 418 (shown as pinchers in this illustrated embodiment) configured to receive a user input to control movement of the arm 300 and configured to be freely moved around by the user U (e.g., handheld and moved around any space in or near an operating room, etc.), an additional arm 422 that can be configured and used similar to the arm 300, and a control system 426 configured to facilitate control of the arms 300, 422 by transferring user inputs received from the user input devices 412, 418, e.g., manual movement of a user input device, movement indicated by touch on a touch screen, etc., to one or both of the arms 300, 422 as appropriate. The system 406 in this illustrated embodiment includes two arms 300, 422, but it can include any number of arms, e.g., three, four, etc. The display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can include at least one computer 428, one or more cables 430, and at least one power supply 432. The computer 428 can include at least one processor (not shown). As mentioned above, some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device.

The robotic surgical system 406 can further include a frame 424 for each of the arms 300, 422. The frames 424 in the illustrated embodiment are each mounted to a surgical table 426, but as mentioned above, frames can be mounted elsewhere. The frames 424 in the illustrated embodiment each include a vertical extension movably coupled to a rail mounted to the table 426. The vertical extension can be configured to move along the rail, thereby facilitating positioning of the arms 300, 422 relative to the patient P.

One or more manually operated surgical instruments 420, e.g., instruments not under the control of the robotic surgical system 406, can also be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
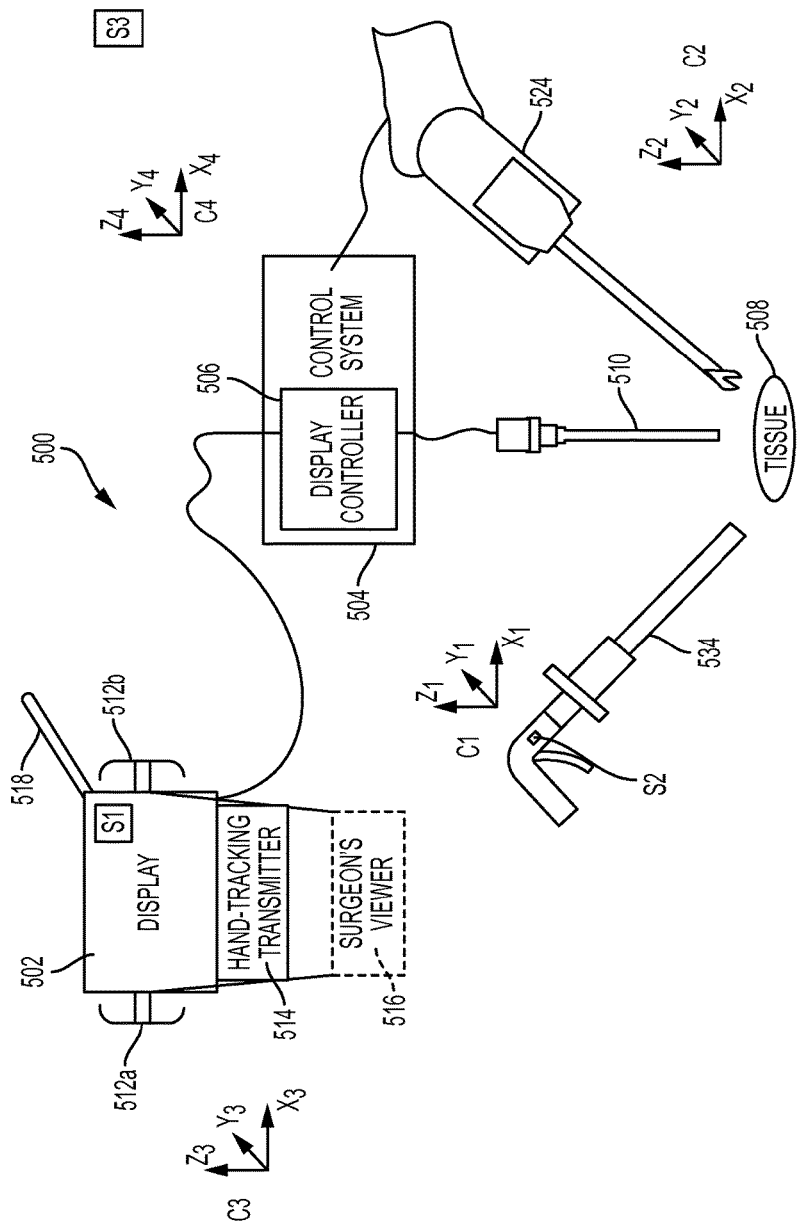
FIG. 9 is a schematic and perspective view of another embodiment of a robotic surgical system having a manually operable instrument and a robotically controlled instrument.

FIG. 9 illustrates another embodiment of a robotic surgical system 500. In this embodiment, the robotic surgical system 500 includes a display 502 and a control system 504 configured to be in electronic communication with the display 502. The display 502 and the control system 504 are shown in wired electronic communication, but the electronic communication can be wireless. The control system 504 can include a computer system having a display controller 506 configured to facilitate the display of images on the display 502, such as images of tissue 508 visualized by an endoscope 510 coupled to the control system 504. The display 502 can include handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
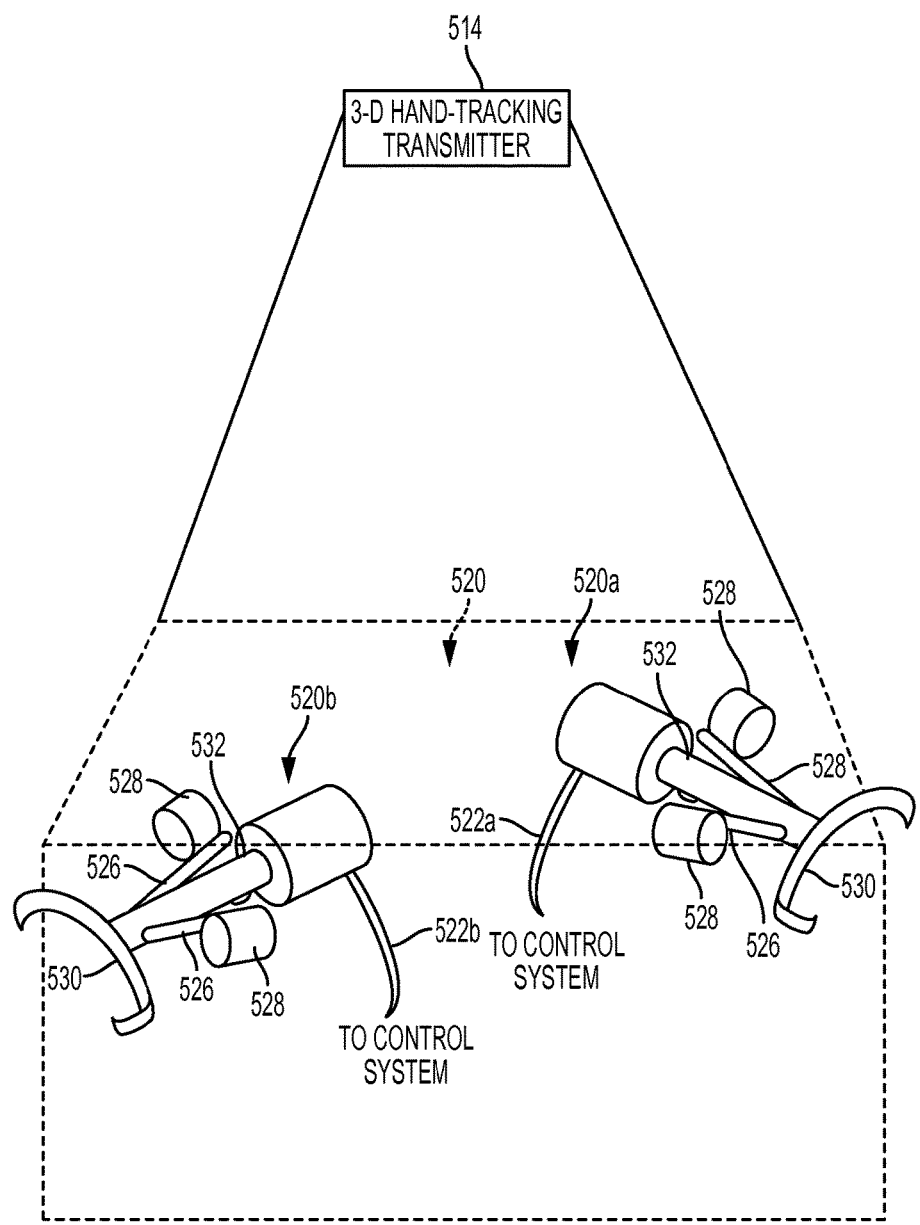
FIG. 10 is a perspective view of one embodiment of a user input device positioned in a field generated by a transmitter of the robotic surgical system of FIG. 9.

Movement of a user-controlled master tool 520 in a field generated by the transmitter 514 can be configured to provide sensed spatial position and orientation information in a 3-D coordinate system, as shown in FIG. 10. The master tool 520 can be configured to transmit the spatial position and orientation information to the control system 504, such as by cables 522a, 522b or using a wireless transmission. The control system 504, e.g., a processor thereof, can be configured to receive the transmitted spatial position and orientation information and, in response thereto, it can cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 504, and hence also with images that the control system 504 and the display controller 506 cause to be displayed on the display 502. In general, the control system 504 can be configured to transfer the third coordinate system C3 into the second coordinate system C2, e.g., transfer movement of the master tool 520 to movement of the slave tool 524. Mapping can be accomplished by, for example, an algorithm such as the Jacobian Matrix.

First, movement of the master tool 520 in the field generated by the transmitter 514, as discussed above, can be mapped into 3-D coordinates within the third coordinate system C3. For example, if the user is holding the master tool 520, e.g., one of the first and second master tool grips 520a, 520b, in one of his/her hands and moves that hand to his/her right, thereby moving the held master tool 520 to the right, this movement will be mapped into 3-D coordinates X3, Y3, Z3 within the third coordinate system C3. These movement coordinates can be communicated to the control system 504. The control system 504 can be configured to correspondingly transfer this movement from the third coordinate system C3 into the second coordinate system C2. For example, the control system 504 can transfer the 3-D coordinates X3, Y3, Z3 of the third coordinate system C3 into 3-D coordinates X2, Y2, Z2 of the second coordinate system C2. The control system 504 can then cause a working end of the slave tool 524 to move to the right by moving the slave tool 524 to the newly translated 3-D coordinates X2, Y2, Z2 of the second coordinate system C2. As the coordinates in the third coordinate system C3 change in coordination with movement of the master tool, the coordinates in the second coordinate system C2 will likewise simultaneously change, thereby causing the slave tool to move in coordination with the master tool. Thus the slave tool 524 effectively mimics the movement of the master tool 520. This movement is referred to herein as mimicked movement or motion. If the master tool 520 moves to the right, the slave tool 524 will move to the right, mimicking the movement. This movement can be accomplished by the control system 504 causing an arm to which the slave tool 524 is coupled, similar to the arms discussed herein, to move. The control system 504 and the display controller 506 can be configured to orient an image in the display 502 to the third coordinate system C3.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument," which is incorporated herein by reference.

Mirrored/Mimicked Switches

Figure 11:
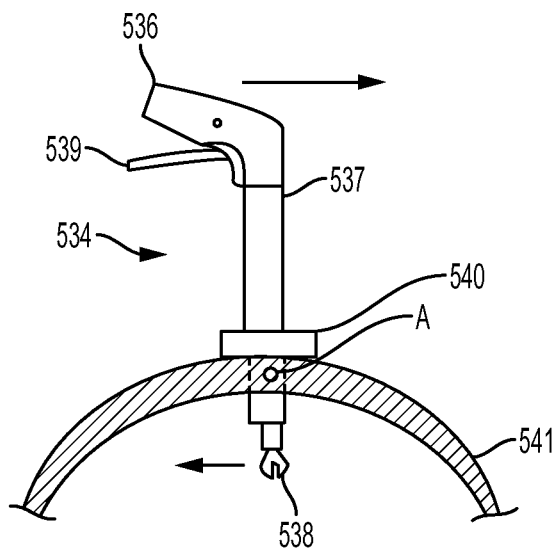
FIG. 11 is a perspective view of the manual surgical tool of FIG. 9 shown disposed within a trocar.

A potential problem can arise when a user is required to manipulate both a manually operated surgical instrument and a master tool concurrently during an operation. FIG. 11 illustrates the manually operated surgical instrument 534 of FIG. 9. The manually operated surgical instrument 534 includes a handle 536 with a trigger 539. An elongate shaft 537 extends distally from the handle 536 and has an end effector 538 at a distal end thereof. The end effector 538 can be actuated by pulling the trigger 539. During minimally invasive surgery, the elongate shaft and end effector can be inserted into a patient through a trocar 540. The trocar 540 allows access to the interior tissue of a patient through the patient's body wall 541. The point at which the shaft 537 passes through the tissue wall is referred to herein as the surgical access point A. With the end effector 538 positioned within a body cavity of a patient, movement of the handle 536 of the manually operated surgical instrument 534 will result in a corresponding movement of the end effector 538 within the patient's body. However, as represented by the arrows in FIG. 11, movement of the handle 536 in one direction will cause the end effector 538 to move in an opposite direction. In other words, movement of the end effector 538 will mirror, not mimic, the movement of the handle 536. Such mirrored movement of the end effector 538 is due to pivoting of the instrument at the surgical access point A. The movements mirror each other across the center of rotation (located at the access point A) of the elongate shaft 537. Thus if the user is holding the handle 536 in one of his/her hands and moves that hand to his/her right, thereby moving the handle 536 to the right, the elongate shaft 537 rotating at the center of rotation (access point A) within the trocar 540 correspondingly causes the end effector 538 within the patient's body to move to the left. Thus movement of the handle 536 to the right will cause the end effector 538 to move to the left. This motion is referred to herein as mirrored movement or motion.

Figure 12:
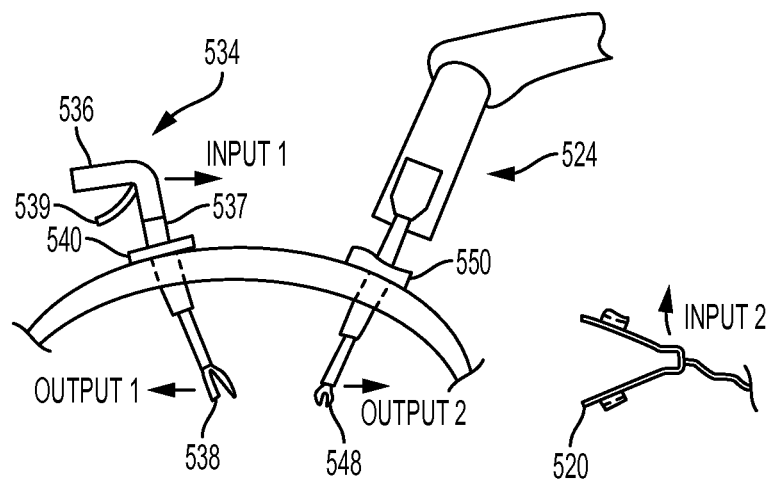
FIG. 12 is a perspective view of a hybrid surgical system having the manually operable instrument of FIG. 11 and the robotically controlled instrument of FIG. 9.

If a user desires to concurrently manipulate both a manually operated surgical instrument and a master tool of a robotic system during an operation, the manual instrument will move with mirrored motion while a slave tool of the master tool will move with mimicked motion. This combination of mirrored and mimicked motion may put a strain on the user during surgery and may thus require extensive, additional training. As shown in FIG. 12, when a user manipulates the handle 536, movement of the handle 536 is translated into a mirrored movement of the end effector 538 because the movement is translated to the end effector through a trocar 540. The user therefore must move the hand grasping the handle 536 in a direction that is opposite to the desired direction of motion of the end effector. At the same time, however, the user may desire to manipulate the master tool 520 with the slave tool 524, which requires the other hand grasping the master tool 520 to move in the same desired direction of motion of the slave tool 524. Accordingly, in one exemplary embodiment, the system can be configured to allow switching from mimicked motion to mirrored motion such that movement of the master tool 520 can selectively cause either mimicked movement by the end effector 548 located at the distal end of the slave tool 524 or mirrored movement by the end effector 548 located at the distal end of the slave tool 524. When hybrid surgery is being performed, i.e. the user is simultaneously operating a manual tool and a robotic tool, the user can operate the handle 536 and the master tool 520 in the same manner to cause mirrored movement of the end effectors 538, 548 (as shown by the arrows in FIG. 12). While an exemplary embodiment is discussed herein, a person skilled in the art will appreciate that it is for illustrative purposes and these techniques can be applied to any and all of the instruments and devices discussed throughout.

In order to allow switching so that a user does not have to combine both movement patterns and to mentally compensate for mirrored movement in one hand and mimicked movement in the other hand, the control system 506 of FIG. 9 can be configured to reverse the second coordinate system C2 such that the mapped motion in the third coordinate system, when transferred to the second coordinate system, is reversed. This can be achieved by simply reversing the second coordinate system. Thus the mapped movement of the master tool 520 is transferred to produce mirrored movement of the slave tool 524 rather than a mimicked movement. This reverse mapping can result in similar mirrored movement between the slave tool 524 and the manually operated surgical instrument 534. Movement in the second coordinate system C2 can thus be reversed from movement in the third coordinate system C3 such that movement within the second coordinate system C2 of the slave tool 524 will be mirrored as with movement of the manually operated instrument 534 within the first coordinate system C1 of the slave tool 524.

Alternating between direct movement in the second coordinate system C2 to cause mimicked movement of the slave tool 524 and reversed movement in the second coordinate system C2 to cause mirrored movement of the slave tool 524 can be achieved through activation of a switch by the user. Activation of the switch can send a signal to the control system 504 to cause the control system 504 to reverse the second coordinate system C2 such that the mapped movement transferred from the third coordinate system C3 is applied to the second coordinate system C2 to cause mirrored movement of the slave tool 524. In one embodiment, the mode control button 532 on the master tool 520 can function as the switch to toggle between the two movement processes, as shown in FIG. 10. However, the switch is not required to be placed on the master tool 520 and can be placed anywhere, such as anywhere on the control system 506. For example, the switch can be built into the display 502, such as by a touch-screen button rendered by software S1 or by allowing a user to instruct the processor (not shown). The switch S2 can also be placed on the manual tool 520 and send a signal wirelessly to the control system 506. The switch S3 can also be a separate, independent device, or the switch can be placed on the operating table itself (not shown). The switch can be in the form of a button that a user actuates, a toggle switch, a slide, a trigger, a lever, a knob, or any other form capable of performing as a switch. The switch can also perform multiple actions beyond alternating between the direct movement and reversed movement, such as disabling various sensors or activating functions in the control system 506. For example, some surgical systems require a user to continuously actuate a pressure sensor during operation of the surgical instruments by requiring the user to press his or her head against a pressure sensor at a control station (not shown). The switch can be activated to disable the pressure sensor and allow the user to not continually actuate the sensor during operation of the instruments. Additionally, reversed movement can be returned to direct movement upon further activation of the switch.

In use and as shown in FIG. 12, a user can position the end effector 548 of the slave tool 524 and the end effector 538 of the manually operated surgical instrument 534 within the patient's body through trocars 540, 550. The user can manipulate the master tool 520, which can send a control signal to a control system 504. The control system 504 will map the movement of the slave tool 524 into the third coordinate system C3, and such movement will be transferred to the second coordinate system C2. The control system 504 in turn can send a control signal, corresponding to the mapped movement in the second coordinate system C2, to the slave tool 524. Receipt of the control signal can cause the slave tool 524 to mimic the motion of the master tool 520. For example, motion to the right of the master tool 520 can cause motion to the right of the end effector 548 at the distal end of the slave tool 524 through the control system's direct movement process.

The user can then activate, for example, the mode control button 532 located on the master tool 520. This activation can send a control signal to the control system 504 causing the control system to reverse the second coordinate system C2. The user can then manipulate the master tool 520, which can send a control signal to the control system. The mapped motion from the third coordinate system C3, when transferred to the second coordinate system C2, causes the control system to send a control signal to the slave tool 524 to cause the slave tool 524 to mirror the motion of the master tool 520. Thus, motion to the right of the master tool 520 can cause motion to the left of the end effector 548 at the distal end of the slave tool 524 through the control system's reverse coordinate mapping process. In other words, the end effector 548 will mirror movement of the master tool 520.

Simultaneously with manipulation of the master tool 520, the user can also manipulate the manually operated surgical instrument 534, which manipulation can cause the end effector 538 of the manually operated surgical instrument 534 to move in a mirrored motion relative to the handle 536 of the manually operated surgical instrument 534. This mirrored motion can cause a motion to the right of the handle 536 to be translated to a motion to the left of the end effector 538 at the distal end of the manually operated surgical instrument 534 through pivoting of the elongate shaft 537 at a center of rotation (access point A) at the trocar 540. A user can switch from mimicked motion to mirrored motion at any time during a surgical procedure when the user intends to use both the robotically controlled tool and the manually controlled tool. When the manual tool is not being used, the robotic tool can be operated in the mimicked motion mode.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
an electromechanical tool;
an electronic control system in electronic communication with the electromechanical tool, the control system being configured to control operation of the electromechanical tool;
a controller actuable to communicate a control signal to the electromechanical tool via the electronic control system to operate the electromechanical tool; and
a switch;
wherein the electromechanical tool has a first mode of operation in which the electromechanical tool mimics movement of the controller, and a second mode of operation in which the electromechanical tool mirrors movement of the controller; and
wherein the switch is configured to switch the electromechanical tool between the first and second modes, and the switch is configured to disable one or more sensors upon activation.

2. The surgical system of claim 1, wherein the switch is located on the controller.

3. The surgical system of claim 1, wherein the switch is located on a display.

4. The surgical system of claim 1, wherein the controller is configured to wirelessly transmit the control signal.

5. A surgical system, comprising:
an electromechanical tool;
an electronic control system in electronic communication with the electromechanical tool, the control system being configured to control operation of the electromechanical tool;
a controller actuable to communicate a control signal to the electromechanical tool via the electronic control system to operate the electromechanical tool, the electronic control system being configured to record movement of the controller and being configured to reverse the recorded movement of the controller; and
a switch;
wherein the electromechanical tool has a first mode of operation in which the electromechanical tool mimics movement of the controller such that the electromechanical tool follows the recorded movement of the controller, and a second mode of operation in which the electromechanical tool mirrors movement of the controller such that the electromechanical tool follows the reverse recorded movement of the controller; and
wherein the switch is configured to switch the electromechanical tool between the first and second modes, and the switch is configured to disable one or more sensors upon activation.

6. The surgical system of claim 5, wherein the switch is located on the controller.

7. The surgical system of claim 5, wherein the switch is located on a display.

8. The surgical system of claim 5, wherein the controller is configured to wirelessly transmit the control signal.

9. A surgical system, comprising:
an electromechanical tool;
a controller configured to be manipulated by a user;
a control system electronically engaged with the electromechanical tool and the controller, the control system being configured to map movement of the controller directly to a mimicked coordinate system; and
a switch;
wherein the control system is configured to cause the electromechanical tool to move according to the mapped movement of the mimicked coordinate system, and the control system is configured to cause the electromechanical tool to move according to a mirrored coordinate system that reverses the mimicked coordinate system; and
wherein the switch is configured to switch the electromechanical tool between the mimicked and mirrored coordinate systems, and the switch is configured to disable one or more sensors upon activation.

10. The surgical system of claim 9, wherein the switch is located on the controller.

11. The surgical system of 9, wherein the switch is located on a display.

12. The surgical system of claim 9, wherein the controller is configured to wirelessly transmit the control signal.

* * * * *